United States Patent
Mahajan

(10) Patent No.: US 9,981,039 B2
(45) Date of Patent: May 29, 2018

(54) COMPOSITION, ITS PREPARATION AND METHOD OF USE IN TREATING SKIN DISORDERS

(71) Applicant: ACCOLADE PHARMA LLC, Wilmington, DE (US)

(72) Inventor: Amey Mahajan, Charlotte, NC (US)

(*) Notice: Subject to any disclaimer, the term of this patent is extended or adjusted under 35 U.S.C. 154(b) by 0 days. days.

(21) Appl. No.: 14/999,576

(22) Filed: May 26, 2016

(65) Prior Publication Data

US 2016/0354469 A1 Dec. 8, 2016

Related U.S. Application Data

(60) Provisional application No. 62/230,185, filed on May 29, 2015.

(51) Int. Cl.
| | |
|---|---|
| *A61K 47/10* | (2017.01) |
| *A61K 31/404* | (2006.01) |
| *A61K 47/14* | (2017.01) |
| *A61K 9/00* | (2006.01) |
| *A61K 9/06* | (2006.01) |

(52) U.S. Cl.
CPC ............ *A61K 47/10* (2013.01); *A61K 9/0014* (2013.01); *A61K 9/06* (2013.01); *A61K 31/404* (2013.01); *A61K 47/14* (2013.01)

(58) Field of Classification Search
CPC ...... A61K 31/404; A61K 47/10; A61K 47/14; A61K 9/0014; A61K 9/06
See application file for complete search history.

(56) References Cited

U.S. PATENT DOCUMENTS 6,440,994 B1 8/2002 Sanders

FOREIGN PATENT DOCUMENTS

| WO | WO 1999 032125 | 7/1999 |
| WO | WO 2005 089748 | 9/2005 |
| WO | WO 2005 089761 | 9/2005 |
| WO | WO2008/106081 | * 9/2008 |
| WO | WO 2009 137555 A1 | 11/2009 |

OTHER PUBLICATIONS

Remington, published 1995, Chapter: Ointments pp. 1585-1691 ).*
G. Riccioni et al., "Advances in Therapy with Antileukotriene Drugs," Annals of Clinical + Laboratory Science, vol. 34, No. 4, 2004, pp. 379-387.
J.A. Bernstein et al., "The effect of oral leukotriene antagonist, ICI-204,219, on leukotriene $D_4$ and histamine-induced cutaneous vascular reactions in man," J. Allergy Clin. Immunol., Jan. 1991, pp. 93-98.
J.A. Carruci et al., "The Leukotriene Antagonist Zafirlukast as a Therapeutic Agent for Atopic Dermatitis," Arch Dermatol., vol. 134, Jul. 1998, pp. 785-786.
E.J. Dabowski et al., "Treatment of atopic dermatitis with Zafirlukost," Dermatology Online. Journal 5(2), https://escholarship.org/uc/item/589055t9.

* cited by examiner

*Primary Examiner* — Savitha M Rao
(74) *Attorney, Agent, or Firm* — Karin J. Karel

(57) ABSTRACT

This invention pertains to a zafirlukast-containing composition, a method of preparing the composition, and a method for treating certain skin disorders using the zafirlukast-containing composition.

8 Claims, No Drawings

COMPOSITION, ITS PREPARATION AND METHOD OF USE IN TREATING SKIN DISORDERS

RELATED APPLICATION

This application claims priority under 35 U.S.C. section 119(e) from Provisional Application No. 62/230,185 filed May 29, 2015, which is hereby incorporated in its entirety.

FIELD OF THE INVENTION

This invention pertains to a zafirlukast-containing composition, a method of preparing the composition, and a method for treating certain skin disorders using the zafirlukast-containing composition.

BACKGROUND

Zafirlukast has the chemical name 4-(5-cyclopentyloxy-carbonylamino-1-methyl-indol-3-ylmethyl)-3-methoxy-N-o-tolylsulfonylbenzamide. It is known to be practically insoluble in water, slightly soluble in methanol, and freely soluble in tetrahydrofuran, dimethylsulfoxide and acetone.

Zafirlukast is a leukotriene receptor antagonist that blocks the action of cysteinyl leukotrienes on the CysT1 receptors, reducing constriction of the airways, build-up of mucus in the lungs and inflammation of the breathing passages. Zafirlukast is commercially available, for example under the brand name ACCOLATE™, and is commonly used to treat asthma.

The use of zafirlukast to treat skin disorders has also been disclosed, both by oral and topical treatment methods. Topical treatments have the advantage of delivering the active pharmaceutical ingredient only to those areas in need of such treatment.

U.S. Pat. No. 6,440,994 claims a method of treating skin disorders such as acne vulgaris, acne rosacea, acne conglobata and hidrandenitis suppurativa by administering a therapeutically effective amount of a leukotriene receptor antagonist such as zafirlukast. An oral treatment method is disclosed.

WO 1999032125 claims a pharmaceutical composition comprising at least one leukotriene antagonist (e.g., zafirlukast) and at least one antihistamine. A method is also claimed for treating diseases of the skin by administering the pharmaceutical composition to a mammal. Skin diseases include atopic dermatitis, psoriasis and chronic idiopathic urticaria. Preferably, the pharmaceutical composition is designed for oral administration.

WO 2005089761 claims a pharmaceutical composition containing a combination of a leukotriene receptor antagonist (e.g., zafirlukast) and a histamine H3 receptor ligand. A method is claimed for treating an H3 mediated disease and/or a leukotriene mediated disease by administering the pharmaceutical composition. A method for treating dermatitis is claimed. Topical administration to the skin is disclosed. Typical carriers include alcohol, water, mineral oil, liquid petrolatum, white petrolatum, glycerin, polyethylene glycol and propylene glycol.

WO 2005089748 claims a pharmaceutical composition containing a combination of a leukotriene receptor antagonist (e.g., zafirlukast) and a histamine H receptor ligand. A method is claimed for treating an H4 mediated disease and/or a leukotriene mediated disease by administering a pharmaceutical composition comprising an effective amount of a leukotriene antagonist and an effective amount of a histamine H4 receptor antagonist. A method for treating dermatitis is claimed. Topical administration to the skin is disclosed. Typical carriers include alcohol, water, mineral oil, liquid petrolatum, white petrolatum, glycerin, polyethylene glycol and propylene glycol.

US 2011/0124681 discloses a method of treating dermatological conditions by administering a topical formulation comprising at least one leukotriene antagonist, e.g., zafirlukast. The "dermatological conditions" include wrinkling of the skin, eczema, uneven texture of the skin, hyperpigmentation, and scarring caused by conditions such as acne, including adult rosacea, or "adult acne." Preferred topical dosage forms include aerosols, gels, solutions, lotions, creams, ointments and foams. Topical ointment formulations are disclosed, which may variously comprise petrolatum, zinc oxide, vegetable oils, animal fats, semisolid hydrocarbons obtained from petroleum, hydroxystearin sulfate, anhydrous lanolin, hydrophilic petrolatum, cetyl alcohol, glyceryl monostearate, lanolin, polyalkylsiloxanes, stearic acid, and/or polyethylene glycols of varying molecular weight. Additional active components may include additional active agent, excipients, solvents, emulsifiers, chelating agent, surfactants, emollients, permeation enhancers, preservatives, antioxidants, lubricants, pH adjusters, adjuvants, dyes, and perfumes. The Example discloses a topical formulation comprising zafirlukast, propylene glycol, ethanol, water and glycerin.

G. Riccioni et al. have reviewed the use of leukotriene receptor antagonist drugs in diseases in which leukotrienes play a pathogenic role. It is noted that several studies documented that combined therapy with montelukast and zafirlukast produced significantly greater improvements than placebo or cetirizine monotherapy in the treatment of chronic urticaria. ("Advances in Therapy with Antileukotriene Drugs," Annals of Clinical & Laboratory Science, vol. 34, no. 4, 2004, pp 379-387)

J. A. Bernstein et al. assessed the antagonism of $LTD_4$-induced cutaneous vascular reaction in man by ICI-204,219 (zafirlukast). They state that it is believed that leukotrienes may participate in the pathogenesis of nonallergic and allergic cutaneous diseases. They also note that it remains to be demonstrated whether an $LTD_4$ antagonist, such as ICI-204,219 (zafirlukast), will have clinical use for management of selected cases of urticaria or psoriasis. ("The effect of the oral leukotriene antagonist, ICI-204,219, on leukotriene $D_4$ and histamine-induced cutaneous vascular reactions in man," J. Allergy Clin. Immunol., January 1991, pp 93-98)

J. A. Carruci et al. disclose treatment of atopic dermatitis using oral administration of zafirlukast. ("The Leukotriene Antagonist Zafirlukast as a Therapeutic Agent for Atopic Dermatitis," ARCH DERMATOL., Vol. 134, July 1998, pp 785-786)

E. J. Dabowski et al. also disclose the treatment of atopic dermatitis with oral zafirlukast. ("Treatment of atopic dermatitis with zafirlukast," Dermatology Online Journal, 5 (2), https://escholarship.org/uc/item/589055t9)

Topical formulations are typically most effective when the pharmaceutical agent is soluble in the formulation. Although zafirlukast is known to be soluble in solvents such as tetrahydrofuran, dimethylsulfoxide and acetone, such solvents are typically not recommended or are contraindicated for use in topical formulations because of concerns for toxicity and/or volatility. There remains, therefore, a need for a safe and effective zafirlukast-containing composition for treating dermatological conditions.

SUMMARY OF THE INVENTION

One aspect of this invention is a composition comprising:
a. zafirlukast;

b. a first and a second polyethylene glycol;
c. a nonionic hydrophilic ester;
d. an alcohol; and
e. an antioxidant.

Another aspect of this invention is a method for treating skin disorders comprising administering to a patient in need of treatment a composition comprising:
a. zafirlukast;
b. a first and a second polyethylene glycol;
c. a nonionic hydrophilic ester;
d. an alcohol; and
e. an antioxidant.

Another aspect of this invention is a process for preparing a composition comprising:
a. forming a first mixture by dissolving zafirlukast in a mixture of a nonionic hydrophilic ester and a first polyethylene glycol;
b. forming a melted phase by heating a mixture comprising the first polyethylene glycol, a second polyethylene glycol, and an alcohol;
c. dissolving an antioxidant in the melted phase to form a third mixture;
d. adding the first mixture to the third mixture while agitating; and
e. cooling the combined first and third mixture while maintaining agitation.

DETAILED DESCRIPTION

A composition used as a topical treatment for skin disorders must satisfy several criteria, such as efficacy, storage stability, safety, and should also possess certain desirable aesthetic qualities.

Ointments, including non-aqueous ointments, are often preferred for efficacy since they are occlusive and can lead to good skin penetration of the active ingredients. Ointments help improve skin hydration by reducing trans-epidermal water loss and result in good compliance; as they are well-tolerated in compromised skin.

Storage stability is related to several factors, but generally refers to the tendency of the components of the formulation to react with each other and/or oxygen, water or other chemicals present in the environment. Antioxidants can improve storage stability.

Safety is related to attaining an efficacious concentration in and on the skin without attaining blood levels associated with efficacious oral dosing.

Desirable aesthetic qualities can include ease of use and the "look and feel" of the ointment. Desirable characteristics can include smoothness of the ointment, appropriate level of color and/or transparency, and low, or at least pleasant, fragrance.

Efficacy of an ointment is also related to the amount of the pharmaceutically active ingredient (API) present in the ointment and more particularly, to the concentration of dissolved API. Surprisingly, it has been found that certain combinations of solvents have a synergistic effect on the solubility of zafirlukast and that these combinations prevent the crystallization of zafirlukast during storage.

One embodiment of this invention is a composition comprising: zafirlukast; a first and a second polyethylene glycol; a nonionic hydrophilic ester; an alcohol; and an antioxidant. In some embodiments, the composition is a zafirlukast-containing ointment.

Zafirlukast (CAS 107753-78-6) is commercially available in powder form. Zafirlukast is known to exist in several polymorphic forms, all of which are suitable for use in the compositions and preparation methods described herein.

Suitable first polyethylene glycols include polyethylene glycol 400, which is available commercially.

Suitable second polyethylene glycols include polyethylene glycol 1450, which is available commercially.

Suitable nonionic hydrophilic esters include PEG 6 caprylic/capric glycerides, which is available commercially under the trade name "glycerox 767."

Suitable alcohols include stearyl alcohol, which is available commercially.

Suitable antioxidants prevent or minimize the discoloration of the zafirlukast-containing composition and include butylated hydroxytoluene (BHT), tert-butyl hydroquinone (TBHQ), butylated hydroxy anisole, and propyl gallate, all of which are available commercially. In some embodiments, the antioxidant is TBHQ. In some embodiments, the antioxidant is BHT.

In some embodiments, zafirlukast comprises 0.1-1 weight percent of the composition, the first polyethylene glycol comprises 50-65 weight percent of the composition, the nonionic hydrophilic ester comprises 4-5 weight percent of the composition, the second polyethylene glycol comprises 24-35 weight percent of the composition, the alcohol comprises 2-8 weight percent of the composition, and the antioxidant comprises 0.001-0.02 weight percent of the composition.

In some embodiments, the composition is an ointment comprising 0.1-1 weight percent zafirlukast, 50-65 weight percent polyethylene glycol 400, 4-5 weight percent glycerox 767, 24-36 weight percent polyethylene glycol 1450, 2-8 weight percent stearyl alcohol, and 0.001-0.02 weight percent antioxidant. In some embodiments, zafirlukast comprises 0.1-0.5 weight percent of the ointment.

In some embodiments, the composition further comprises additional active agents, excipients, solvents, emulsifiers, chelating agents, surfactants, emollients, permeation enhancers, preservatives, lubricants, pH adjusters, adjuvants, dyes, or perfumes.

In some embodiments, the viscosity of the composition is 15,000-60,000 centipoise per second (cPs) at a shear rate of 10 reciprocal seconds. In some embodiments, the viscosity is 30,000-60,000 centipoise per second (cPs) at a shear rate of 10 reciprocal seconds.

One aspect of this invention is a method for preparing a composition, wherein the process comprises:
a. forming a first mixture by dissolving zafirlukast in a mixture of a nonionic hydrophilic ester and a first polyethylene glycol;
b. forming a melted phase by heating a mixture comprising the first polyethylene glycol and a second polyethylene glycol and an alcohol;
c. dissolving an antioxidant in the melted phase to form a third mixture;
d. adding the first mixture to the third mixture while agitating; and
e. cooling the combined first and third mixture while maintaining agitation.

Forming the first mixture to dissolve the zafirlukast can be facilitated by heating the mixture of zafirlukast, nonionic hydrophilic ester and first polyethylene glycol to a temperature between 40° C. and 75° C. Similarly, the melted phase can be formed by heating the first and second polyethylene glycols and the alcohol to a temperature between 40° C. and 75° C.

The disclosed method is useful in preparing a zafirlukast-containing ointment.

The disclosed composition can be used to treat leukotriene-mediated skin disorders, including disorders such as acne vulgaris, acne rosacea, acne conglobata, hidrandenitis suppurative, atopic dermatitis, chronic idiopathic urticaria, eczema, and burns, including sunburn and radiation burns. Treatment comprises applying the zafirlukast-containing composition to the area of the skin affected by the skin disorder as needed. Typically, the composition is applied one or multiple times per week, one or multiple times a day, or as prescribed. Treatment of some skin disorders may benefit by treating areas of the skin adjacent to the perilesional areas exhibiting redness, swelling, bumps, pimples or other lesions. Typically, the composition is applied as an ointment.

EXAMPLES

Unless stated otherwise, all weights are given as weight percents, based on the total weight of the composition.

Example 1

Preparation of a Zafirlukast-Containing Ointment, Stabilized with TBHQ

Zafirlukast (1.00%) was added to a mixture of glycerox 767 (5.00%) and polyethylene glycol 400 (20.00%), which was then stirred until the zafirlukast dissolved. A separate mixture of polyethylene glycol 400 (39.98%), polyethylene glycol 1450 (29.00%), and stearyl alcohol (5.00%) was heated to 60° C. until melting occurred, followed by the addition of tert-butyl hydroquinone (0.02%). This was stirred until the TBHQ completely dissolved. After the TBHQ-containing phase was gradually cooled to 50° C., the zafirlukast-containing mixture was added with agitation. The combined mixture was gradually cooled to 30° C. with agitation.

The initial viscosity was 44,510 cPs. After six weeks at 25° C., it was 38,630. After six weeks at 40° C., it was 16,060. No significant color change was observed, even after six weeks at 40° C.

Example 2

Preparation of a Zafirlukast-Containing Ointment, Stabilized with BHT

The preparation of Example 1 was repeated, except that butylated hydroxytoluene (0.025%) was substituted for TBHQ and the amount of polyethylene glycol 400 was reduced to 59.975%.

The initial viscosity was 37,310 cPs. After six weeks at 25° C., it was 47,860 cPs. After six weeks at 40° C., it was 16,140 cPs. No significant color change was observed, even after six weeks at 40° C.

Example 3

Preparation of a Zafirlukast-Containing Ointment, Stabilized with Butylated Hydroxy Anisole The preparation of Example 1 was repeated, except that butylated hydroxyanisole (0.005%) was substituted for TBHQ and the amount of polyethylene glycol 400 was increased to 59.995%.

The initial viscosity was 40,570 cPs. After six weeks at 25° C., it was 49,290 cPs. After six weeks at 40° C., it was 22,140 cPs. No significant color change was observed, even after six weeks at 40° C.

Example 4

Preparation of a Zafirlukast-Containing Ointment, Stabilized with Propyl Gallate The preparation of Example 1 was repeated, except that propyl gallate (0.015%) was substituted for TBHQ and the amount of polyethylene glycol 400 was increased to 59.985%.

The initial viscosity was 41,160 cPs. After six weeks at 25° C., it was 57,520 cPs. After six weeks at 40° C., it was 22,800 cPs. No significant color change was observed, even after six weeks at 40° C.

I claim:
1. A method for preparing a composition, comprising:
   a. forming a first mixture by dissolving zafirlukast in a mixture of a nonionic hydrophilic ester and a first polyethylene glycol;
   b. forming a melted phase by heating a mixture comprising the first polyethylene glycol, a second polyethylene glycol, and an alcohol;
   c. dissolving an antioxidant in the melted phase to form a third mixture;
   d. adding the first mixture to the third mixture while agitating; and
   e. cooling the combined first and third mixture while maintaining agitation, wherein said nonionic hydrophilic ester is PEG 6 caprylic/capric glycerides.
2. The method of claim 1, wherein the composition is a zafirlukast-containing ointment.
3. The method of claim 1, wherein the composition is non-aqueous.
4. The method of claim 1, wherein the first mixture is non-aqueous.
5. The method of claim 1, wherein the first polyethylene glycol is polyethylene glycol 400.
6. The method of claim 5, wherein the second polyethylene glycol is polyethylene glycol 1450 and the alcohol is stearyl alcohol.
7. The method of claim 1, wherein the antioxidant is selected from the group consisting of butylated hydroxytoluene, tert-butyl hydroquinone, butylated hydroxy anisole, and propyl gallate.
8. The method of claim 7, wherein the antioxidant is tert-butyl hydroquinone.

* * * * *